United States Patent [19]

Davis

[11] 4,115,483

[45] Sep. 19, 1978

[54] PROCESS FOR PREPARING MONO-ALKYL ACID PHOSPHATES HAVING HIGH MONO-CONTENT AND LIGHT COLOR

[75] Inventor: Gershon Jerry Davis, White Plains, N.Y.

[73] Assignee: Stauffer Chemical Company, Westport, Conn.

[21] Appl. No.: 827,192

[22] Filed: Aug. 23, 1977

[51] Int. Cl.$^2$ .............................................. C07F 9/09
[52] U.S. Cl. ...................................... 260/980; 260/963
[58] Field of Search ........................................ 260/980

[56] References Cited

U.S. PATENT DOCUMENTS

| 2,586,897 | 2/1952 | Woodstock | 252/135 |
| 2,701,258 | 2/1955 | Brown et al. | 260/980 |
| 3,318,982 | 5/1967 | Knapsack et al. | 260/980 |

Primary Examiner—Anton H. Sutto
Attorney, Agent, or Firm—William R. Robinson

[57] ABSTRACT

Mono-alkyl acid phosphates having the formula:

$$ROP(OH)_2 \quad \overset{O}{\underset{\|}{}} \quad (I)$$

wherein R is straight or branched alkyl having from 1 to about 25 carbon atoms, are prepared by reacting alcohol with $P_2O_5$ in the presence of tetrasodium pyrophosphate and hydrogen peroxide. The process involves initially adding $P_2O_5$ to a mixture of alcohol and tetrasodium pyrophosphate followed by continuous or sequential addition of water and hydrogen peroxide, $P_2O_5$ (in stoichiometic excess) and then alcohol. Additional hydrogen peroxide is added at the end of the reaction. A mixture of mono- and di-alkyl acid phsophate is obtained with a mono-content of over about 70 percent by weight.

5 Claims, No Drawings

PROCESS FOR PREPARING MONO-ALKYL ACID PHOSPHATES HAVING HIGH MONO-CONTENT AND LIGHT COLOR

BACKGROUND OF THE INVENTION

1. Field of the Invention

The present invention relates, in general, to a process for preparing mono-alkyl acid phosphates, and particularly concerns an improved process for preparing said phosphates with a high mono-content and light color.

2. The Prior Art

Mono-alkyl acid phosphates are well-known, and are generally prepared by reacting alcohols with phosphorus pentoxide. The nature of the chemical reaction between alcohols and phosphorus pentoxide is very non-discreet. The result, therefore, is a mixture of products including monoalkyl acid phosphate, di-alkyl acid phosphate, free phosphoric acid, variously substituted pyrophosphate, and possibly even triphosphate. The situation is further complicated in the case wherein stearyl alcohol is used as it is a solid at room temperature and relatively unreactive. Phosphorus pentoxide is also a solid. Therefore, the reaction between stearyl alcohol and phosphorus pentoxide must be run at a temperature above the melting point of stearyl alcohol (mp 58° C.).

It is particularly advantageous to obtain a product according to the present invention that is high in mono-content. The high mono-content product is more effective than low mono-content products as a surfactant and as an agent for removal of blood stains, egg yolk, and the like from cloth and other materials.

Another advantage of the present invention is the light color of the product. Light color is advantageous because it makes the product more desirable for marketing purposes.

Various methods have been described in the prior art for improving the mono-content in the synthesis of mono-alkyl acid phosphates. In U.S. Pat. No. 2,586,897, for example, water is added to the reaction mixture of lauryl alcohol and phosphorus pentoxide to hydrolyze any acid phosphate esters. This enhances the production of monolauryl phosphate. This technique is also described in U.S. Pat. No. 3,318,982.

It is also known in the prior art to add hydrogen peroxide to the reaction mixture to improve the color of the product. See, for example, U.S. application Ser. No. 791,625, filed Apr. 27, 1977.

SUMMARY OF THE INVENTION

In accordance with the present invention, production of mono-alkyl acid phosphates with high mono-content and light color is achieved by following a specific reaction sequence.

The sequence is generally outlined as follows:

Step 1. — Alcohol is introduced into a reaction vessel followed by mixing with tetrasodium pyrosphosphate.

Step 2. — An approximately stoichiometric amount of $P_2O_5$ is introduced into the reaction vessel.

Step 3. — Water and hydrogen peroxide, $P_2O_5$ and alcohol are introduced sequentially or continuously into the reaction vessel. The $P_2O_5$ added at this time is in slight stoichiometric excess over the alcohol.

Step 4. — Hydrogen peroxide is introduced into the reaction vessel.

The product is a mixture of mono- and di-alkyl acid phosphate having light color and a mono-content of over about 70 percent by weight.

The products of the present invention have the general formula:

wherein R is straight or branched alkyl having from 1 to about 25 carbon atoms.

An idealized reaction scheme for the present invention is:

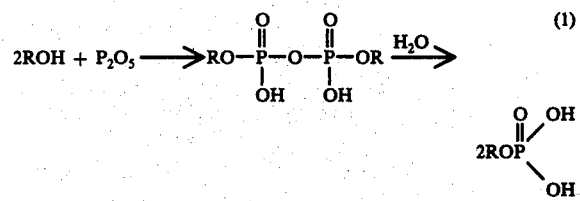

wherein R is as defined above.

DETAILED DESCRIPTION OF THE INVENTION

In the mono-alkyl acid phosphates of the present invention having the structural formula:

wherein R is as defined above, exemplary R groups include but are not limited to methyl, ethyl, propyl, isopropyl, butyl, tert-butyl, pentyl, heptyl, octyl, decyl, dodecyl, hexadecyl, nonadecyl, lauryl, palmityl and stearyl.

The process of the present invention is carried out by following a specific reaction sequence. Said sequence can be defined by four sequential steps as follows:

Step. 1. — Alcohol having the structural formula:

ROH                                    (II)

wherein R is as defined above, is introduced into a reaction vessel. Tetrasodium pyrophosphate ($Na_4P_2O_7$) is admixed with the alcohol, prior to or following introduction of the alcohol into the reaction vessel, in an amount from about 0.1 percent to about 0.5 percent by weight of the alcohol.

Step 2. — An approximately stoichiometric amount of phosphorus pentoxide ($P_2O_5$) is introduced into the reaction vessel.

Step 3. — Water and hydrogen peroxide, the hydrogen peroxide having a concentration from about 5 percent to about 10 percent by weight of the water, $P_2O_5$ and the alcohol are introduced sequentially or continuously into the reaction vessel.

The $P_2O_5$ added in this step is in stoichiometric excess from about 2 percent to about 15 percent over the alcohol.

Step 4. — Hydrogen peroxide in an amount from about 0.2 percent to about 0.5 percent by weight of the alcohol is introduced into the reaction vessel.

The following reaction scheme (2) is representative of the process:

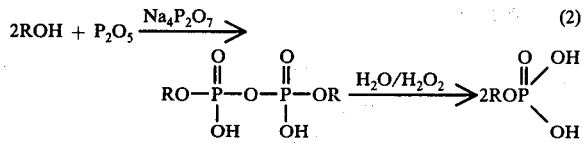

(2)

wherein R is defined above.

Step 1 can be modified by utilizing a heel from a previous preparation of mono-alkyl acid phosphate rather than the initial charge of alcohol. The heel generally consists of mono-alkyl acid phosphate, di-alkyl acid phosphate and free $H_3PO_4$. This modification has the disadvantage that the product is darker than the product produced with an initial charge of alcohol to the reaction vessel.

A stoichiometric excess of $P_2O_5$ is utilized in Step 3 to limit the quantity of di-alkyl acid phosphate formed.

The final step of adding hydrogen peroxide results in a lighter colored product.

Products of the process can be removed from the reaction vessel by, for example, pumping the product to a flaker followed by discharging the resultant flakes into a storage or shipping container.

During Steps 1 and 2, the temperature of the reactants in the reaction vessel is maintained from about 20° to about 180° C., and preferably from about 50° to about 100° C. The preferred temperature range is selected because excess thermal energy will promote undesirable side reactions such as dehydration which results in the formation of pyro-compounds and other reactions which are deleterious to the color of the mono-alkyl acid phosphate product. Inadequate thermal energy, however, can result in crystallization or solidification of the alcohol. Process temperatures that will provide good product distribution and color can easily be determined by one skilled in the art.

In Steps 3 and 4, the reaction mixture is maintained at a temperature from about 40° to about 200° C., and preferably from about 60° to about 140° C. The reason for the preference is to minimize thermal catalyzed degradation which is accompanied by lower yields, undesired product color even with the addition of hydrogen peroxide, and possible loss of desired product selectivity. The optimum temperature can easily be determined by one skilled in the art. In the case of a process utilizing stearyl alcohol, for example, the optimum temperature is in the range from about 80° to about 85° C.

The product is a mixture of mono-alkyl acid phosphate and di-alkyl acid phosphate having a mono-content of over about 70 percent by weight.

The reaction can be conducted in a continuous or batchwise process.

Reaction times can vary over relatively wide ranges and can easily be determined by one skilled in the art. Factors affecting reaction time include reaction temperature, viscosity, efficiency of mixing, rate of addition of reactants and rate of heat input.

Typical reaction times are from about 1 to about 10 hours. Times from about 3 to about 6 hours are preferred, however, to prevent product degradation and color formation.

The products of the present invention can be purified if desired by conventional means. These include crystallization and chromatography among others.

The identification of the products can be achieved by infrared spectroscopy, hydrogen and phosphorus nuclear magnetic resonance spectroscopy, titration, and elemental analysis.

Typical yields of the desired mono-alkyl acid phosphates of the present invention are from about 70 percent to about 95 percent.

Illustrative of the mono-alkyl acid phosphate compounds of the present invention are:

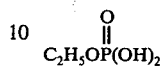

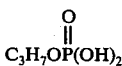

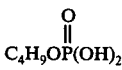

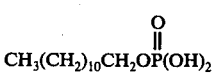

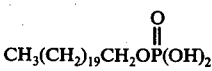

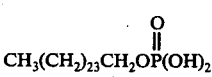

Isomers of the foregoing illustrative compounds are also illustrative of the mono-alkyl acid phosphate compounds of the present invention.

The mono-alkyl acid phosphates of the present invention are useful as surface active agents for use in cleaning systems such as detergents utilized in dish-washing and industrial bottle-cleaning formulations, food grade lubricants and flotation and suspending agents.

One aspect of the present invention involves the preparation of monostearyl acid phosphate. The reaction to produce this product requires the use of molten stearyl alcohol in the process described above, or use of solid stearyl alcohol flakes added to the reaction mixture.

The present invention will be more fully illustrated in the example which follows:

EXAMPLE

Pilot plant scale equipment was utilized to prepare monostearyl acid phosphate. The equipment was as follows:

1. a jacketed, 300 gallon, stainless steel reactor provided with a turbine agitator, baffles and a thermocouple;

2. a 20 gallon per minute stainless steel centrifugal pump provided on a recycling line for the reactor, the pump and line having steam coils;

3. a variable speed, stainless steel, screw feeder provided with a 30 cubic foot hopper and placed on a scale;

4. a variable feed, single drum, flaker having a 12 inch diameter and an 18 inch length; and 5. an open, 50 gallon, stainless steel container provided with a steam coil.

Raw materials utilized were as follows:

1. stearyl alcohol flakes;
2. phosphoric anhydride (P$_2$O$_5$);
3. food grade tetrasodium pyrophosphate;
4. 30% hydrogen peroxide; and
5. deionized water.

The process was conducted stepwise as follows:

1. Two hundred pounds of stearyl alcohol flakes were added to the 50 gallon container. The system was turned on to melt the alcohol flakes while maintaining temperature below 90° C. Melting time was two hours.

2. The liquid stearyl alcohol was then transferred to the 300 gallon reactor and the turbine agitator was turned on. The steam was then turned off.

3. Two pounds of tetrasodium pyrophosphate were added to the reactor.

4. The steam was turned on or the steam coils in the recycling line and pump. After the coils heated up, the bottom valve on the reactor was opened and the pump turned on.

5. The steam was then turned off and cold water was circulated through the jacket to bring the stearyl alcohol temperature down to 80° C.

6. Fifty-five pounds of P$_2$O$_5$ was then added to the reactor at a rate of 1 to 1.5 pounds per minute. The temperature was maintained at 80° to 85° C. throughout the addition. When the temperature reached 85° C., 3600 cubic centimeters of water mixed with 360 cubic centimeters of H$_2$O$_2$ was added in small portions over a span of about 20 minutes. This helped to keep the temperature of the reaction mixture below 85° C.

7. After the water addition, the P$_2$O$_5$ feeding was stopped as soon as the reaction temperature reached 85° C. Small increments of P$_2$O$_5$ were then added as the temperature went down until the entire 55 pounds of P$_2$O$_5$ was added.

8. The jacket temperature was then adjusted to 85° C. with warm water and the following series of operations were performed twelve times.
   (a) The reaction temperature was maintained at 80°-85° C.
   (b) 900 cubic centimeters of water mixed with 90 cubic centimeters of 30% H$_2$O$_2$ were added to the reactor and at the same time 14 pounds of P$_2$O$_5$ were added at a rate of 1 pound per minute.
   (c) As soon as 1-2 pounds of P$_2$O$_5$ had been added, the addition of 50 pounds of stearyl alcohol was begun. The addition of P$_2$O$_5$ was kept proportionally ahead of the stearyl alcohol addition.
   Steps (a) – (c) took a total of about 20 minutes. Over the entire reaction period, the mass of reaction looked like a tan to light brown fluid slurry. No foaming occurred.

9. Once all of the raw materials had been added, the reactor contents were agitated for 2 more hours and kept at 80° to 85° C. The slurry became a clear brown liquid.

10. Bleaching was then effected by adding 2000 cubic centimeters of 30 percent H$_2$O$_2$. Agitating was then continued for 2 hours and the liquid became a tan color.

11. The product was removed from the reactor by the following procedures:
    (a) The pipe from the reactor was heated with a steam coil.
    (b) The flaker pan was heated with a steam coil and an electrical heater.
    (c) The flaker drum was cooled with cool water and the drum speed was set at 4 revolutions per minute.
    (d) Flow through the reactor pipe was begun and maintained at a rate of about 120 pounds per hour.

Easily breakable sheets of product were obtained from the flaker drum. During the flaking procedure, 30 percent H$_2$O$_2$ was added to the reactor every two hours in an H$_2$O$_2$ equivalent of about 0.1 percent of the product still left in the reactor.

The major components of the product had the following specifications:

78 percent monostearyl acid phosphate (1050 pounds)
8.8 percent distearyl acid phosphate
7.0 percent phosphoric acid
color — off-white flakes Having set forth the general nature and an example of the present invention, the scope is now particularly set forth in the appended claims.

I claim:

1. A process for preparing mono-alkyl acid phosphates having the formula:

wherein R is straight or branched alkyl having from 1 to about 25 carbon atoms, comprising the steps of (1) first contacting an alcohol having the formula:

wherein R is as defined above, with tetrasodium pyrophosphate in an amount from about 0.1 percent to about 0.5 percent by weight of said alcohol at a temperature from about 20° C. to about 180° C.; (2) followed by contacting an approximately stoichiometric amount of P$_2$O$_5$ with the alcohol-tetrasodium pyrophosphate mixture at a temperature from about 20° to about 180° C. and mixing; (3) followed by contacting water and hydrogen peroxide, P$_2$O$_5$ in stoichiometric excess, and alcohol to the mixture of step (2) at a temperature from about 40° to about 200° C.; and (4) mixing at a temperature from about 40° to about 200° C. until the reaction is complete and then finally adding hydrogen peroxide to the reaction mixture followed by additional mixing.

2. The process of claim 1 wherein the hydrogen peroxide admixed in step (3) has a concentration from about 5 percent to about 10 percent by weight of the water admixed in step (3).

3. The process of claim 1 wherein the P$_2$O$_5$ admixed in step (3) is in stoichiometric excess from about 2 percent to about 15 percent over the alcohol.

4. The process of claim 1 wherein the hydrogen peroxide admixed in step (4) is in an amount from about 0.2 percent to about 0.5 percent by weight of the total alcohol utilized.

5. The process of claim 1 wherein R is selected from the group consisting of methyl, ethyl, propyl, isopropyl, butyl, tert-butyl, pentyl, heptyl, octyl, decyl, dodecyl, hexadecyl, nonadecyl, lauryl, palmityl, and stearyl.

* * * * *